United States Patent
Völkert et al.

(10) Patent No.: US 8,785,695 B2
(45) Date of Patent: Jul. 22, 2014

(54) METHOD FOR PURIFYING COMPOUNDS CONTAINING AMINO GROUPS

(75) Inventors: Martin Völkert, Ludwigshafen (DE); Burkhard Ernst, Speyer (DE); Wolfgang Siegel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/515,883

(22) PCT Filed: Dec. 13, 2010

(86) PCT No.: PCT/EP2010/069523
§ 371 (c)(1), (2), (4) Date: Jun. 14, 2012

(87) PCT Pub. No.: WO2011/082976
PCT Pub. Date: Jul. 14, 2011

(65) Prior Publication Data
US 2012/0253076 A1    Oct. 4, 2012

(30) Foreign Application Priority Data

Dec. 17, 2009 (EP) ..................... 09179624

(51) Int. Cl.
*C07C 209/84* (2006.01)
(52) U.S. Cl.
USPC .......................................... 564/498; 564/499
(58) Field of Classification Search
USPC .................................. 564/498, 499
See application file for complete search history.

(56) References Cited

U.S. PATENT DOCUMENTS

| 1,898,461 | A | * | 2/1933 | Nicodemus et al. | 564/499 |
| 4,174,351 | A | * | 11/1979 | Shoffner | 564/425 |
| 4,582,937 | A | * | 4/1986 | Hiraga et al. | 564/498 |
| 4,683,337 | A | * | 7/1987 | Budde | 564/498 |
| 5,189,221 | A | * | 2/1993 | Duranleau et al. | 564/499 |
| 5,481,037 | A | * | 1/1996 | Fuchs et al. | 564/437 |
| 6,011,156 | A | * | 1/2000 | Matson | 546/184 |
| 6,353,138 | B1 | * | 3/2002 | Rooney | 564/497 |
| 2010/0292429 | A1 | | 11/2010 | Volkert et al. | |

FOREIGN PATENT DOCUMENTS

| EP | 1482055 A1 | 12/2004 |
| JP | 2004000114 A | 1/2004 |
| JP | 2004222569 A | 8/2004 |
| WO | WO-2009092793 A2 | 7/2009 |

OTHER PUBLICATIONS

International Preliminary Report on Patentability from PCT/EP2010/069523 dated Jul. 4, 2012.
U.S. Appl. No. 12/864,176, filed Jul. 22, 2010, Volkert et al.
International Search Report for PCT/EP2010/069523 mailed Jun. 6, 2011.

* cited by examiner

*Primary Examiner* — Brian J Davis
(74) *Attorney, Agent, or Firm* — Drinker Biddle & Reath LLP

(57) ABSTRACT

Method for purifying compounds (I) containing amino groups from a polar phase A, where
(I) is converted by reaction with an aldehyde or ketone (II) into the corresponding imine (III) which is insoluble or sparingly soluble in the polar phase A, and
then the imine (III) is converted to a nonpolar phase B and separated off from phase A, and
then the compound containing amino groups is recovered from the imine (III).

8 Claims, No Drawings

METHOD FOR PURIFYING COMPOUNDS CONTAINING AMINO GROUPS

RELATED APPLICATIONS

This application is a national stage application (under 35 U.S.C. §371) of PCT/EP2010/069523, filed Dec. 13, 2010, which claims benefit of European Patent Application No. 09179624.3, filed Dec. 17, 2009.

The present invention relates to a method for purifying compounds containing amino groups, in particular alkylamines or alkyldiamines, which are present together with impurities and by-products in a polar phase. Of particular suitability is the method for purifying compounds containing amino groups which have been prepared by fermentation and which, at the end of the preparation process, are present in an aqueous phase together with constituents of the fermentation medium.

BACKGROUND OF THE INVENTION

Compounds containing amino groups are important basic substances in the chemical industry. For example, alkylamines and alkyldiamines are used in the production of polyamides, polyureas or polyurethanes and also copolymers thereof.

The fermentative or enzymatic production of alkyldiamines, for example of diaminopentane (DAP) by decarboxylation of lysine has been known for a relatively long time. In this connection, various methods for isolating the product of value from the fermentation broth are described.

Thus, for example, EP-A-1 482 055 describes the enzymatic decarboxylation of lysine in the presence of a dicarboxylic acid for establishing the pH during the reaction. The DAP dicarboxylate produced during the preparation is isolated by firstly decoloring the solution containing substance of value with activated carbon, concentrating it and crystallizing out DAP dicarboxylate by means of a cooling crystallization.

JP 2004-222 569 describes the preparation of DAP using an L-lysine decarboxylase-expressing coryneform bacterium, adjustment of the culture supernatant to pH 12 and extraction of DAP with a polar organic solvent.

JP 2004-000 114 describes the preparation of DAP by reacting highly concentrated L-lysine monohydrochloride with L-lysine decarboxylase-expressing *E. coli* cells, adjusting the reaction solution to pH 3 and extraction of the reaction product with a polar organic solvent and subsequent distillation.

WO 2009/92793 describes a method for isolating 1,5-diaminopentane (DAP) from a DAP-containing fermentation broth, where the fermentation broth is a) alkalized, b) thermally treated, c) DAP is extracted with an organic extractant, and d) DAP is isolated from the separated-off organic phase.

However, particularly the methods known from the prior art and based on an extraction of DAP with the help of an organic solvent are burdened with the disadvantage that the yield of substance of value is not optimal and especially the extraction step proceeds too slowly and the overall method is therefore too time-consuming, which is a major disadvantage for application of the preparation on an industrial scale.

SUMMARY OF THE INVENTION

The object of the present invention is therefore to further improve the isolation of compounds containing amino groups from fermentation broths. In particular, the yield of substance of value should be further increased and the required time expenditure for the isolation, in particular the solvent-based extraction, should be improved.

Surprisingly, this object has been achieved through provision of a method for purifying compounds (I) containing amino groups from a polar phase A, where
i) (I) is converted through reaction with an aldehyde or ketone (II) into the corresponding imine (III) which is insoluble or sparingly soluble in the polar phase A and
ii) then the imine (III) is transferred to a nonpolar phase B and
iii) is separated off from phase A, and
iv) then the compound containing amino groups is recovered from the imine (III).

DETAILED DESCRIPTION OF THE INVENTION

Preferred Embodiments

The invention provides a method for purifying compounds (I) containing amino groups from a polar phase A, where
i) (I) is converted through reaction with an aldehyde or ketone (II) into the corresponding imine (III) which is insoluble or sparingly soluble in the polar phase A and
ii) then the imine (III) is transferred to a nonpolar phase B and
iii) is separated off from phase A, and
iv) then the compound containing amino groups is recovered from the imine (III).

In a first specific embodiment of the method for purifying compounds (I) containing amino groups, alkyl derivatives which carry one or more, preferably two or three, amino functions are used as (I). In particular, mention may be made here of alkyl derivatives having 1 to 10 carbon atoms, which may be present in linear, branched or cyclic form. The method is particularly advantageously used for diaminoalkyls, such as diaminopropane, diaminobutane, diaminopentane, diaminohexane, diaminoheptane and diaminooctane. In these specified compounds, the two amino groups may be in any arrangement relative to one another, but are preferably in 1,n position for a diamino-n-alkyl, i.e. 1,3-diaminopropane, 1,4-diaminobutane, 1,5-diaminopentane etc.

Such diaminoalkyls are prepared by methods known to the person skilled in the art. A preparation process which is used advantageously for diamines such as 1,5-diaminopentane is the fermentative or enzymatic preparation.

Here, at the end of the preparation process, the compound (I) containing amino groups is usually present in an aqueous fermentation medium in which, besides compound containing amino groups and, if appropriate, by-products and starting materials, also constituents of the nutrient medium and also metabolic products are present. Such an aqueous fermentation medium is referred to for example as polar phase A. Other examples of polar phases A are water or aqueous solutions or polar organic solvent such as lower alkyl alcohols or lower carboxylic acids or mixtures of these polar organic solvents with water.

The compounds containing amino groups are generally readily soluble in aqueous phases, especially at a low pH as a consequence of (partial) protonation.

The compounds (I) containing amino groups are converted through reaction with an aldehyde or ketone (II) to the corresponding imine (III). (II) is advantageously selected such that the formed (III) is insoluble or only sparingly soluble in the polar phase A in which (I) is located.

The reaction of (I) with (II) to give (III) can be carried out in a wide temperature range, preference being given to temperatures between 20 and 50° C. The imine formation is improved by adding a base since, as the result of this, the position of the equilibrium is shifted to the (III) side.

As aldehyde or ketone (II), it is possible to use any desired aliphatic or aromatic aldehydes and ketones which are capable of diimine formation with compounds carrying amino groups. Those compounds (II) which reduce the solubility of the imines (III) to be formed in the polar phase A in which the compounds containing amino groups are located are advantageous.

Preferred aldehydes or ketones (II) are benzaldehyde, valeraldehyde, cyclohexanone, methyl ethyl ketone, diisobutyl ketone, 2-octanone and acetone, where, for the imine formation from 1,5-diaminopentane, benzaldehyde is particularly preferred.

The aldehyde or ketone (II) is usually used in equimolar amounts or a slight excess (1-1.5 preferably 1-1.1 equivalents) based on the amino groups in the compounds (I) containing amino groups, in order to achieve a quantitative imine formation (III).

However, since the aldehydes or ketones (II) can also serve as solvents for the imines (III), it is also possible to use (II) in a large excess based on (I) and then to separate off the formed imines (III) in (II) as solvent.

In a step iii) of the method according to the invention, the formed imine (III) is transferred to a nonpolar phase B. Nonpolar phase B is understood as meaning a phase which is not to a noteworthy extent miscible with the polar phase A, and preferably forms a phase separation to phase A.

Besides the aforementioned compounds (II), nonpolar phase B can also nonpolar organic solvents such as ethers, medium- and relatively long-chain alcohols, hydrocarbons, ketones, aldehydes, aromatics.

Nonpolar phase B can be added as early as at the start of step ii); however, it is also possible to carry out step ii) without further solvents and only to add a nonpolar phase B after imine formation (III) has taken place.

In a further step iii), the nonpolar phase B, which comprises the imine (III), is separated off from the polar phase A. This step is preferably carried out as an extraction and can be operated continuously or discontinuously. Preference is given to a discontinuous extraction at elevated temperature, i.e. between 30° and 70° C.

In one preferred embodiment, the extraction and/or the subsequent phase separation is carried out discontinuously at elevated temperature, the temperature being limited by the boiling points of water and of the extractant and/or azeotropes that are possibly formed. Using n-butanol as extractant, extraction and phase separation could be carried out e.g. at about 25-90° C. or preferably at 40-70° C. For the extraction, the two phases are stirred until the partition equilibrium has been established, e.g. over a period from 10 seconds to 2 hours, preferred 5 to 15 min. The phases are then left to stand until the phases have completely separated; this takes place preferably over a period of 10 seconds to 5 hours, such as e.g. 15 to 120 or 30 to 90 minutes, in particular also at a temperature in the range of about 25-90° C. or 40-70° C. in the case of n-butanol.

The design in terms of apparatus of the extraction columns which can be used according to the invention can be established by the person skilled in the art for the phases to be separated in each case in the course of routine optimization work. Of suitability in principle are extraction columns without power input or extraction columns with power input, such as e.g. pulsed columns or columns with rotating internals. The person skilled in the art can also, in the course of routine work, select the type and materials of internals, such as sieve trays, and column packings, for optimizing the phase separation in a suitable manner. The theoretical principles of liquid-liquid extraction of small molecules are generally known (cf. e.g. H.-J. Rehm and G. Reed, Eds., (1993), Biotechnology, Volume 3 Bioprocessing, Chapter 21, VCH, Weinheim). The configuration of industrially applicable extraction columns is described for example in Lo et al., Eds., (1983) Handbook of Solvent Extraction, John Wiley & Sons, New York. Reference is expressly made to the disclosure of the above textbooks.

The phase separation required for a successful extraction can be positively influenced by changing the pH in the polar phase A. As a rule, pH values of >12 achieve optimal mass transfer into the nonpolar phase B.

If desired; after separating off the imine (III) from the polar phase A, it can be further purified or concentrated at the imine stage, for example by distillation, chromatography or crystallization.

In a last step iv), the compounds (I) containing amino groups are recovered from the imines (III). This back-reaction of the imine formation takes place advantageously with the addition of acid, it being possible to use here mineral acids or organic acids. The back-reaction of the imine formation takes place particularly readily with an equimolar addition of acid. Step iv) can be carried out by means of steam distillation.

A particular embodiment uses those acids which can form polyamides in a subsequent process with the compounds (I) containing amino groups. Here, as a result of the purification according to the invention of the compound (I) containing amino groups, the monomeric "preproduct" consisting of carboxylic acid and compound (I) containing amino groups can be simultaneously provided for the still to be prepared polyamides. This embodiment is preferably in the case of diaminoalkylene as (I) which are to be reacted with dicarboxylic acids to give polyamides. Nonlimiting examples of suitable dicarboxylic acids are succinic acid, glutaric acid, adipic acid, pimelic acid, suberic acid, azelaic acid, sebacic acid.

In the case of the compound containing amino groups 1,5-diaminopentane, preferred acids for this embodiment are sebacic acid and adipic acid.

General information relating to the fermentative preparation of 1,5-diaminopentane (DAP)

As regards the fermentative preparation of 1,5-diaminopentane, reference is made to WO 2009/92793. The experiments described below refer to the DAP obtained in this way by fermentation.

The fermentation broths, particularly those containing L-lysine or DAP, obtained in this way usually have a dry mass of from 3 to 20% by weight.

The fermentation broth is then further processed. Depending on requirements, the biomass can be completely or partly removed from the fermentation broth by separation methods, such as e.g. centrifugation, filtration, decantation, flocculation or a combination of these methods, or be left entirely therein. Preference is given to separating off the biomass.

The fermentation broth can then be thickened or concentrated using known methods, such as e.g. with the help of a rotary evaporator, thin-film evaporator, falling-film evaporator, by reverse osmosis, or by nanofiltration. If required, any salts precipitated out by the concentration can be separated off for example by filtration or centrifugation. The concentrated fermentation broth can then be worked-up in the manner according to the invention in order to obtain DAP. For the work-up within the context of the present invention, such a concentration is possible, but not absolutely necessary.

Experimental Part

Formation of Imine for the Purification of DAP

The imine formation (FIG. 1 using benzaldehyde as the example) proceeds with the elimination of water. As a consequence of the pH regulation in the fermentation, DAP is present in the broth as sulfate, which leads during the imine formation to the reduction in the pH and shifts the reaction back to the starting material side. This makes the addition of a base necessary in order to bring the reaction to completion.

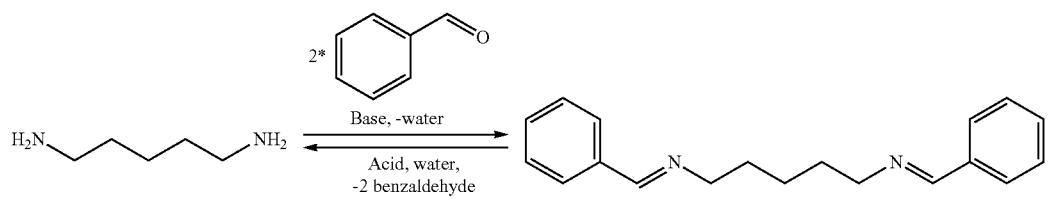 [SMILES: NCCCCCN ; O=Cc1ccccc1 ; C(=N\CCCCC/N=C/c1ccccc1)/c1ccccc1]

FIG. 1 Imine Formation

With benzaldehyde, the spontaneous deposition of an organic product phase was observed. In principle, the reaction was successful with the stoichiometric amount of benzaldehyde and then led to products of up to 98.5 area % GC purity.

During the extraction of an alkaline fermentation broth with methyl ethyl ketone, a mixture of imine, diaminopentane and water was deposited. Phase separation was extraordinarily good in this experiment. From the mixture it was possible to back-cleave diaminopentane through a steam distillation with removal of the azeotrope (but without defined reflux); it was largely retained in the bottom.

The following were used successfully: cyclohexanone, methyl ethyl ketone (MEK), diisobutyl ketone, benzaldehyde, valeraldehyde, 2-octanone, methyl isoamyl ketone, methyl isobutyl ketone.

Imine Formation with Benzaldehyde

In an experiment to determine the required amount of base, 212 g of fermentation broth with a DAP content of 6% were admixed with 2 eq. of benzaldehyde and the product distribution and the pH were determined as a function of the added amount of NaOH (fig.). For this, after adding the respective amount of NaOH, a sample was taken, the phases were separated and the aqueous and organic phases were analyzed by GC and quantitative HPLC.

It was found that after adding 20 g of NaOH, the conversion was virtually complete (benzaldehyde virtually consumed, barely DAP in the water phase, GC of the upper phase 92.5% diimine); here, a pH of 9.4 had been established in the mixture. Based on the PMDA present in the fermentation broth, this corresponds to a feed number of ca. 0.8 kg NaOH/kg DAP 100% strength, and is thus somewhat more favorable than in the case of the extractive work-up, but is nevertheless in the same order of magnitude. An experiment for the continuous extraction of the diimine from a fermentation broth in the rotary perforator initially proceeded with difficulty due to a very sluggish distillation on account of the high boiling point of the benzaldehyde (180° C.), although it was found that at a pH of 5.85, which is rapidly established after adding the benzaldehyde, virtually no diimine could be extracted.

In the 4 l miniplant reactor, from 4 kg of fermentation broth (pH 13.5, DAP content 6.78% by weight) with the addition of 2 eq. of benzaldehyde, the desired imine could be isolated quantitatively in high purity (753 g, 98.4 area % GC). Phase separation took place spontaneously, but was only complete after 48 h—barely half of the product settled out from the water phase even during this time.

Apparatus: 4 l miniplant reactor, with pH probe and pH meter
Mixture: 4053.0 g of DAP broth GC % by wt. 6.78 corresponds to 274.8 g of DAP 2.7 mol
572.9 g of benzaldehyde (5.4 mot, 2 eq)
Reaction: The fermentation broth was introduced as initial charge at RT (stirrer 400 rpm). The benzaldehyde is then metered in over the course of one hour. Stirred overnight. pH 13. Has not changed during the reaction.
Work-up: The phases were separated. Organic phase (753.4 g), aqueous phase (3880 g). 330 g of this organic phase was separated only after ca. 48 h.
Analytics: GC: method GC9-06-K.M imine 98.4 area %

In general, during the imine formation, states emulsified with benzaldehyde are passed through, and only after largely complete reaction is the phase separation acceptable again.

In order to improve and increase the rate of phase separation, a series of experiments were undertaken with solvents. For this, alkaline fermentation broths were admixed at room temperature with a mixture of benzaldehyde and the solvent in question and the phases were separated at elevated temperature (Table 1).

TABLE 1

| Ex. No. | Solvent | Amount of solvent | Temp. | Remarks |
|---|---|---|---|---|
| 1 | Cyclohexane | 100% | 50° C. | cloudy phases - clarification only after 48 h |
| 2 | Benzaldehyde | 100% | 60° C. | homogeneous, readily separable |
| 3 | Benzaldehyde | 50% | 60° C. | homogeneous, readily separable |
| 4 | 2-Octanol | 100% | 60° C. | very good phase separation. Incomplete conversion |
| 5 | 1-Hexanol | 100% | 60° C. | very good phase separation, complete conversion |
| 6 | Cyclohexanol | 100% | 60° C. | very good phase separation, complete conversion |
| 7 | Without | | 60° C. | acceptable phase separation, slight mulm |

For cyclohexane and toluene, moreover, experiments were carried out in which, at 50° C., the phase separation time was investigated as a function of the progress of the reaction—controlled via the added amount of NaOH and the benzaldehyde used. Following phase separation, the aqueous phase was replenished in each case through the metered addition of NaOH to pH 10, benzaldehyde and solvent were freshly added, the mixture was stirred for 15 minutes and pH and phase separation times were measured.

With toluene, phase separation times between 27 and 54 seconds were observed, the aqueous phases being cloudy at the start and virtually clear at the end. The first organic phases contained a very stable foam, which did not disintegrate even upon combining the organic phases.

With cyclohexane, the phase separation times were between 35 and 110 seconds. The aqueous phases were generally less cloudy than with toluene, but also in these organic phases, the formation of very stable foams resulted (34224/28).

In a further experiment with 4 eq. of benzaldehyde, the phase separation was investigated depending on the added amount of NaOH. Here, the phase separation remained slow until the pH of 9 was reached and all of the PMDA had reacted to give the imine. This was the case for an amount of 65 g of NaOH (50% strength), based on the PMDA used this corresponds to a feed number of 0.6 kg/kg PMDA.

The organic phase remained foamy until the reaction was complete whereas then phase separation was good.

Cleavage of Imines

The imine formation is an equilibrium reaction in the presence of water, and therefore it was the original idea to manage the back-reaction in such a way that the carbonyl component being released could be removed from the equilibrium as steam-volatile compound by steam distillation. At the same time, the position of the equilibrium is dependent on the pH, which was indeed also observed even during the imine formation.

Benzaldehyde Imines

As a result of a stoichiometric amount of sulfuric acid, the cleavage of the imine takes place smoothly in an aqueous mixture. The back-cleaved benzaldehyde is deposited as an independent organic phase and can be separated off.

As small cleavage experiments, in each case 15-20 g of imine were distilled with water without further additives and also in the presence of in each case 0.5 g of sulfuric acid, Lewatit S 1468 (strongly acidic ion exchanger), Lewatit CNP80 (weakly acidic ion exchanger) and p-toluenesulfonic acid. In this connection, in no case was a cleavage of the imine observed which extended beyond the extent to be expected due to the catalyst acid.

The imine itself could not be distilled at 4 mbar at an oil bath temperature up to 240° C.

Since in the first exploratory experiments, in each case condensed water phases were present which could possibly influence the establishment of an equilibrium, in further experiments at 140-160° C., water was slowly added dropwise or steam was introduced. Here, firstly 5 mol % of sulfuric acid were used as catalyst, and also a comparative experiment without catalyst was carried out. The experiment with the dropwise addition of water foamed to such an extent that some of the distillation bottom was entrained into the distillate initial charge. The experiments with the introduction of steam, on the other hand, proceeded in an uncomplicated manner.

In the presence of 5 mol % of sulfuric acid as catalyst, a mass decrease of the bottom from 117 to 86 g was observed, by GC the diimine to 98.2% by weight. The cloudy distillate (767 g) was extracted with methylene chloride; 4.9% diaminopentane and 7.1% diimine were found in the extract. Ca. 10% of the diimine were thus cleaved and a further 10% were distilled over. It could not be differentiated whether the diimine distills over undecomposed by the steam despite the high boiling point, or whether the diaminopentane distilling over with the benzaldehyde in the initial charge leads to the new formation of the imine. A control experiment for the steam distillation of DAP from aqueous solution revealed that DAP should be retained virtually completely by the attached Vigreux column.

Without added sulfuric acid, 96% of the diimine used (117 g) were recovered, of which 17% were present in the distillate (900 g). In order to be useful in practice, by using a column with higher separation efficiency, the water/benzaldehyde azeotrope must be separated off from the DAP if the diimine is not anyway passed over undecomposed by the steam. In the bottom, no enrichment of free DAP was observed, although analysis is difficult because under the conditions of the HPLC, the diimine is partly back-cleaved to free DAP, but on the other hand the GC method is not able to separate PMDA and benzaldehyde on account of their identical boiling point.

In summary, the benzylidene compound is obviously stabilized so much that the shift in the equilibrium to the starting material side as a result of steam distillation does not take place even in the presence of catalytic amounts of acid.

Since, on the other hand, the back-cleavage was successful through quantitative amounts of acid, it seemed obvious to use, as acid for the cleavage of the imine, the dicarboxylic acid with which the subsequent polymerization is intended. Following the addition of 1 eq. of sebacic acid and steam distillation of the benzaldehyde being released, the sebacate was retained in the bottom. This salt could be further purified by recrystallization from ethanol or butanol. The preparation of the DAP adipate with adipis acid also succeeded in exactly the same way.

In a demonstration experiment, 175 g of imine (prepared from a fermentation broth) with 121 g of sebacic acid in 1200 g of water were subjected to an azeotropic distillation. The remaining residue was taken up in ethanol, adjusted by azeotropic distillation to a water value of <0.3% and a content of ca. 30% strength and crystallized with inoculation at 50° C. and cooling to 40° C. in 2 h, and also to 20° C. in a further 2 h. During the crystallization, the acetyldiaminopentane, which was present in the imine with ca. 1.5%, was depleted by about 213. Ca. 89% of a weakly yellowish colored crystallizate were obtained. Recrystallization from ethanol led to no further improvement in the color. A difficulty observed was that excess sebacic acid precipitates out at too low a temperature. Precise determination of the imine content and accurate adjustment of the stoichiometry are advantageous for achieving a high purity.

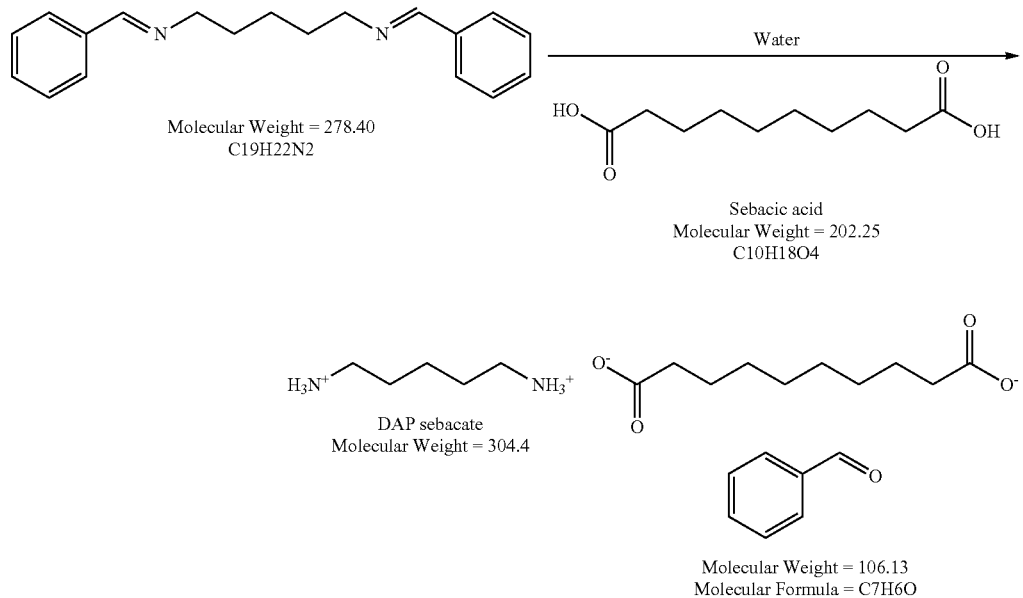

The invention claimed is:

1. A method for purifying a diaminoalkyl compound (I), said method comprising:
   i) preparing said compound (I) by fermentation in an aqueous phase A;
   ii) converting said compound (I) through reaction with an aldehyde or ketone (II) into the corresponding imine (III) which is insoluble or sparingly soluble in the polar phase A;
   iii) transferring the imine (III) to a nonpolar phase B;
   iv) separating off from phase A; and
   v) recovering said compound (I) from the imine (III).

2. The method according to claim 1, wherein the diaminoalkyl is 1,5-diaminopentane.

3. The method according to claim 1, wherein benzaldehyde is used as (II).

4. The method according to claim 2, wherein benzaldehyde is used as (II).

5. The method according to claim 1, wherein step v) is effected by adding an acid.

6. The method according to claim 4, wherein step v) is effected by adding an acid.

7. The method according to claim 5, where the acid is added in equimolar amounts based on (I).

8. The method according to claim 6, where the acid is added in equimolar amounts based on (I).

* * * * *